United States Patent [19]

Johnson

[11] 4,005,194
[45] Jan. 25, 1977

[54] TREATMENT OF PROSTATIC HYPERPLASIA

[75] Inventor: Edwin Samuel Johnson, Antioch, Ill.

[73] Assignee: Abbott Laboratories, Chicago, Ill.

[22] Filed: June 23, 1975

[21] Appl. No.: 589,236

[52] U.S. Cl. .............................................. 424/177
[51] Int. Cl.² ....................................... A61K 37/02
[58] Field of Search .................................... 424/177

[56] References Cited

OTHER PUBLICATIONS

The Merck Manual, 12th Ed., 1972, pp. 669–672.

*Primary Examiner*—Jerome D. Goldberg
*Attorney, Agent, or Firm*—Paul D. Burgauer; Robert L. Niblack

[57] ABSTRACT

A series of nonapeptide amides has been found which, upon administration at daily doses of from about 1–500 µg/kg to male warm-blooded animals, cause regression and subsequent elimination of prostatic hyperplasia without causing adverse effects to healthy tissues.

6 Claims, No Drawings

TREATMENT OF PROSTATIC HYPERPLASIA

DETAILED DESCRIPTION OF THE INVENTION

For a number of years there has been a search for a chemical treatment of warm-blooded animals, who suffer from prostatic disorders; primarily a search was underway to find an orally active agent that causes the regression and/or elimination of hyperplasia without causing substantial adverse effect to other tissue in the host animal.

It has now been found that a series of closely related peptides have the ability to interfere with the metabolism of prostatic tissue to the point of drastically reducing and eventually eliminating the undesirable growth which, in the past, required surgical removal.

The object of this invention is accomplished by administering to a warm-blooded male animal, showing symptoms of an increase in prostatic growth, a sufficient daily dose of a nonapeptide of the formula

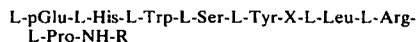

wherein X denotes the optically active D-form of an aminoacid moiety of the formula —NH—CHR'—CO— with R' being a linear or branched carbon chain of 1–4 carbon atoms and wherein R is lower alkyl. The term "lower alkyl" is used to include alkyl groups containing between 1 and 7 carbon atoms. The divalent radical X may be best illustrated by the D-leucyl, D-alanyl, D-valyl or D-isoleucyl moieties. While the described treatment may be effective against other hyperplasia as well, it is primarily directed to the inhibitory effect it has on prostatic growth or hyperplasia.

In a general embodiment, the above nonapeptide is administered to a patient suffering from an unwanted or excessive growth of prostate at a daily dose of between 1 and 500 μg/kg/day as a single daily dose or divided into 2–4 daily doses of the correspondingly smaller amounts. Where oral administration is desired, the dose range is between 2 and 500 μg/kg/day which can easily be exceeded since the compound of formula I does not show any toxic effects at oral does 100 mg/kg. For parenteral administration, a dose of 1–200 μg/kg/day is adequate. The reference to "parenteral" is intended to include all routes of adminstration other than oral; it is particularly directed to intramuscular, subcutaneous, intravenous by injection or infusion, by suppository, by nasal drops, etc. For many of these formulations, solutions of I at a concentration of 5–100 μg/ml in 0.9% saline provide an excellent dosage form. If desired, small amounts of serum albumin may be added to prevent adsorption of I to the glass container in which this dosage form is prepared or stored.

The compound of formula I is highly water-soluble; it can be stored for essentially indefinite periods of time as a solid or as a solution in sterile water or saline. Of course, where desired, buffers such as tris(hydroxymethyl)aminomethane or other pharmaceutically acceptable additives may be included in the solutions before storage or before use.

For oral preparations, any number of pharmaceutical forms can be used, e.g., syrups, elixirs, suspensions or the compound can be processed into wafers, pills, tablets and the like. However, since the dosage required is extremely small, the usual tableting methods require the use of fillers and other excipients to prepare tablets of manageable size. In a preferred embodiment, the oral dosage form consists of a tablet containing between 0.1 and 5.0 mg. of the above peptide per tablet. Such tablets can be coated in the usual fashion, preferably using a readily soluble coating material, e.g., sugar, etc. or the above amount can be incorporated into gelatin capsules which promptly dissolve upon introduction into the stomach. In any event, the usual flavoring and coloring agents can be used without effect on the active peptide so incorporated.

Tablets of this type are prepared in the usual fashion by compounding the active ingedient with starch, granulating the mixture and, after adding the necessary fillers, flavoring agents, lubricants, etc., the mixture is slugged and passed through a 30-mesh screen. The thoroughly blended mixture is then compressed into tablets of desired hardness with the usual punch, preferably to make bisected tablets for easier b.i.d. administration.

In order to show the preparation and use of the compounds of the present invention, reference is made to the following examples which, however, are not intended to limit the invention in any respect. For the purpose of this description, the terms "undesirable growth" or hyperplasia of the prostatic gland are used interchangeably.

EXAMPLE 1

Proline carrying as a blocking group the t-butyloxycarbonyl substituent (elsewhere herein referred to as Boc-) on the amino group is esterified by combining it with a chloromethylated divinylbenzene-styrene copolymer (marketed by Bio-Rad as Merrifield resin) containing 2% of cross linking, using the method described by Stewart, et al. in "SOLID PHASE PEPTIDE SYNTHESIS", (published in 1969 by Freeman & Company), San Franciso, (page 1). In this manner, a resin is produced which by hydrolysis and aminoacid and analysis shows to contain 0.47 millimoles of proline/g. of resin. In an automatic synthesizer developed according to the previously cited Merrifield apparatus, 4.6 g. of this resin/aminoacid matterrial is used for the synthesis of the desired nonapeptide. Each N-blocked aminoacid is added in a three-fold access and allowed to couple to the existing aminoacid-resin ester in the usual coupling cycle. The coupling reaction is carried out for 4.5 hours with continuous shaking and the reaction is subsequently washed six times with methanolchloroform 1:2 for 1.5 minutes each and 4 times with ethanol for 1.5 minutes each. In each instance, a total volume of 48 milliliters is used and the drain time after shaking usually is about 1.5 minutes. After coupling, the mixture is washed four times for 1.5 minutes each with dioxane, twice with 4N hydrochloric acid/dioxane for five minutes and 25 minutes, respectively, five times with dioxane for 1.5 minutes each, three times with ethanol for 1.5 minutes each, three times with chloroform for 1.5 minutes each, three times with 10% triethylamine/-chloroform for 1.5 minutes each, four times with chloroform for 1.5 minutes each and six times with dichloromethane for 1.5 minutes each. Ordinarily the solvent used for the coupling reaction is dichloromethane or, when the solubility of the blocked aminoacid is low, a mixture of dichloromethane and dimethylformamide. Coupling is effected by the addition of a solution of dicyclohexylcarbodiimide in dichloromethane at a 2.9 fold excess.

The sequence used for deprotection, neutralization and coupling of the next aminoacid is done in a fully automatic system as described above. In this manner, the peptide is assembled using in turn Boc-Arg(Tos), Boc-Leu, Boc-D-Leu, Boc-Tyr(Cl$_2$Bzl), Boc-Ser(Bzl), Boc-Trp, Boc-His(DNP), and pGlu wherein all aminoacids are in the L-form except in the leucine so designated.

The resin is removed from the vessel and suspended in 200 ml. of 5% triethylamine/methanol and 100 ml. of distilled ethylamine is added thereto. After 24 hours, the resin is removed by filtration and the solution evaporated to yield a solid. The solid is taken up in glacial acetic acid and applied to a 3 × 50 cm. column of silica gel equilibrated with 5% methanol/chloroform.

The column is eluted with 5% methanol in chloroform until all traces of N-ethyl dinitroaniline, the yellow by-product of the histidine protecting group DNP is removed. The eluant is then changed to 33% methanol/chloroform and fractions of about 30 ml. each are collected. The compound is located by thin-layer chromatography of aliquots of the fractions (Silica gel G. 33% MeOH/CHCl$_3$, Cl$_2$/tolidine spray). The fractions containing the product are pooled and evaporated to give a solid which is precipitated from methanol with ether. This tri-protected nonapeptide (protective groups at Ser, Tyr and Arg) is thus obtained in an amount of 1.69 g., representing an overall yield of 43% of theory.

A 250 mg. sample of the above is placed in a hydrogen fluoride reaction vessel with 250 mg. of anisole and about 5 ml. of anhydrous hydrogen fluoride is distilled into it. After 1 hour at 0° C., the hydrogen fluoride is removed in vacuo, and the residue is taken up in 1% acetic acid. This solution is extracted with ether, and the aqueous phase applied to a 1 × 30 cm. column of a highly basic ion exchange resin (marketed by Bio-Rad as AG1 × 2 resin) in the acetate form. The product is eluted with 0.1 N acetic acid and localized using thin-layer chromatography (CHCl$_3$/MeOH/32% HOAc: 120/90/40, Silica gel G., Cl$_2$/tolidine). The product bearing solution is lyophilized, rechromatographed on a Sephadex G-25 (marketed by Pharmacia of Uppsala, Sweden) column. The product eluted is collected and lyophilized to yield a fluffy while solid $[a]_D^{25} = -31.7°$ (c = 1, 1% HOAc) in a 25% overall yield. Analysis shows the expected ratio of all desired aminoacids assembled in the above fashion. This compound is hereinafter referred to as "Compound N".

When in the above synthesis, the Boc-D-leucine is replaced by the correspondingly protected α-aminobutyric acid, alanine, isoleucine or valine, the above synthesis proceeds in the same fashion, again in all instances, using the automatic synthesizer described above.

EXAMPLE 2

Ten Sprague Dawley male rat 22 days of age and weighing 45–50 grams, were randomly divided into two groups. One group received the treatment described below. After 57 days of treatment, the animals from the non-treatment control group and those from the treatment group were sacrificed. The various organs were removed, trimmed of excess tissue and weighed. Body weights were taken weekly. Group I received no treatment; Group II received 10 μg of Compound N twice each day. The results are shown in Table I with each entry showing the mean value of the respective group.

TABLE I

|  | Group I (Control) |  | Group II |  |
|---|---|---|---|---|
| Ventral Prostate | 379.6 | mg | 211.3 | mg |
| Dorsal Prostate | 198.4 | '' | 113.2 | '' |
| Lateral Prostate | 101.3 | '' | 74.1 | '' |
| Total Prostatic Complex | 679.2 | '' | 398.6 | '' |
| Seminal Vesicles | 745.6 | '' | 292.0 | '' |
| Coagulating Glands | 166.0 | '' | 64.5 | '' |
| Testes | 3401 | '' | 2712 | '' |
| Body weight at onset | 49 | g | 48 | g |
| Body weight after 1 week | 89 | g | 86 | g |
| Body weight after 2 weeks | 136 | g | 139 | g |
| Body weight after 3 weeks | 188 | g | 179 | g |
| Body weight after 4 weeks | 235 | g | 218 | g |
| Body weight after 5 weeks | 271 | g | 252 | g |
| Body weight after 6 weeks | 256 | g | 267 | g |
| Body weight after 7 weeks | 300 | g | 320 | g |
| Body weight after 8 weeks | 342 | g | 346 | g |

The above values show that long-term administration of Compound N to warm-blooded male animals has essentially no effect on their normal weight gain and growth but that it has a profound effect on the development of the male sex organs, blocking excessive growth thereof.

EXAMPLE 3

Male rats, 22 days of age and weighing 45–50 g, were divided into three groups. Group I (control; 10 animals) was given 0.5 ml bid. subcutaneous injections of 0.1% bovine serum albumin in 0.9% saline; Group II (20 animals) received no treatment and Group III (10 animals) received the same as I except that the solution contained 20 μg/ml of compound N. The weight of the animals was taken at intervals for the 105 days of this test. From day 57 to day 105 of treatment, the rats of Group I increased their weight by 28.5%; the rats of Groups II and III gained 22% and 21% respectively. At day 105 of treatment, 5 animals of each group were sacrificed and their organs were weighed. The results are shown in Table II; all numbers given represent the mean value of the 5 animals within each Group.

TABLE II

|  | Group I (Control) |  | Group II (Control) |  | Group III (Treated) |  |
|---|---|---|---|---|---|---|
| Ventral Prostate | 600 | mg | 573 | mg | 386 | mg |
| Dorsal Prostate | 212 | '' | 207 | '' | 136 | '' |
| Lateral Prostate | 103 | '' | 108 | '' | 72 | '' |
| Total Prostatic Complex | 915 | '' | 888 | '' | 593 | '' |
| Seminal Vesicles | 1391 | '' | 1506 | '' | 738 | '' |
| Coagulating Glands | 198 | '' | 200 | '' | 113 | '' |
| Testes | 3630 | '' | 3659 | '' | 3337 | '' |

Table II shows a pronounced and very significant reduction in the weights of those organs and/or glands that are involved in reproduction through the male. The significance of the reduction in weights of the total prostatic complex, the seminal vesicles and coagulating glands are particularly impressive when considered in light of the almost total absence of the change in weight gains between the Groups. Also, no other differences in the animals' appearance and behavior were observed between the Groups. The weight loss in the male reproductive organs is a clear indication that the treatment described above has beneficial effects on pathological conditions that adversely effect the prostatic gland, e.g. prostatic hyperplasia.

EXAMPLE 4

Male rats, 22 days of age, were divided into 3 groups of five animals each. The 3 groups were treated exactly as described in Example 3, but the experiment was continued for 153 days. After 115 days, these animals were bred to untreated, cycling females (each male was caged with 2 cycling females in pro-estrus for 3 consecutive days, on 3–5 separate occasions). The resulting pregnancies progressed normal in all groups and led to healthy pups.

Subsequent to the 153 days of treatment (which includes the breeding period), the male test animals were sacrificed and their organs were weighed (see Table III below) and examined histologically and pathologically.

TABLE III

|  | Group I (Control) | Group II (Control) | Group III (Treated) |
|---|---|---|---|
| Ventral Prostate | 645 mg | 797 mg | 453 mg |
| Dorsal Prostate | 192 " | 213 " | 153 " |
| Lateral Prostate | 125 " | 155 " | 82 " |
| Total Prostatic Complex | 962 " | 1164 " | 688 " |
| Seminal Vesicles | 1596 " | 1789 " | 1046 " |
| Coagulating Glands | 224 " | 228 " | 130 " |
| Testes | 3481 " | 3892 " | 3181 " |
| Epididymis | 1242 " | 1375 " | 1153 " |
| Adrenal Gland | 54.0 " | 56.3 " | 50.9 " |
| Pituitary Gland | 11.5 " | 12.6 " | 12.2 " |

In order to assure that the significant and beneficial changes shown above have no adverse effect on the pups, these pups were observed for several weeks. The results given in Table IV show the average figures for each of the 3 groups.

TABLE IV

|  | Group I | Group II | Group III |
|---|---|---|---|
| Number of pups | 12.9 | 11.4 | 10.4 |
| Weight of pups |  |  |  |
| on day 1 | 6.5 g | 6.6 g | 6.9 g |
| on day 4 | 9.9 " | 10.6 " | 11.7 " |
| on day 11 | 21.4 " | 22.9 " | 23.5 " |
| on day 21 | 36.5 " | 40.3 " | 44.3 " |

The above figures show no statistically significant variations between the pups. The same finding is true also when considering the breeding indices which were determined as a percentage of successful impregnations vs. opportunitites to breed. In Group I, II and III, these indices were 32%, 19% and 23% respectively.

EXAMPLE 5

Thirty adult male Holtzman rats weighing 450–500 g were randomly assigned to one of three groups of 10 animals each. One group (Group II) of rats was orchidectomized to serve as castrate controls. Treatment started 24 hrs after surgery and continued for 21 consecutive days. The animals were sacrificed on the 22nd day and the various organs removed, trimmed of excess tissue and weighed. The results are given as average values in Table V with the treated group receiving 10 μg b.i.d. of Compound N. Groups I and II received 0.1% bovine serum albumin in 0.9% aqueous sodium chloride.

TABLE V

|  | Group I (Control) | Group II (Castrate Control) | Group III (Treated) |
|---|---|---|---|
| Ventral Prostate | 773 mg | 93.4 mg | 763 mg |
| Dorsal Prostate | 214 " | 67 " | 220 " |
| Lateral Prostate | 91 " | 23 " | 83 " |
| Seminal Vesicles | 1230 " | 160 " | 1034 " |
| Total Prostatic Complex | 1078 " | 183 " | 1066 " |
| Coagulating Glands | 212 " | 39 " | 138 " |
| Testes | 3982 " | — | 3350 " |

The above data indicates atrophy in the male reproductive structures.

EXAMPLE 6

In an experiment similar to that of Example 5 with Groups I and III being treated as shown, but Group II being treated like Group III except with only 1 μg of Compound N, the test was continued for 51 days, starting with 22-day old male rats, 5 animals per group. The animals were sacrificed on day 52. The total mean prostatic complex weights were found to be 979 mg for the control group, 936 mg for the low-dose group and 786 mg for the 10 μg b.i.d. group (Group III).

Another three groups of 5 male rats were treated in the identical fashion, but the treatment was extended from the age of 22 days to day 138 (116 days). The mean weights of the prostatic complexes were found to be 1078 mg for Group I, 988 mg for Group II and 875 mg for Group III, showing that even with the lower dose level, a significant inhibition of growth of secondary sex organs can be achieved. None of the treated animals in this experiment showed any outward signs or organic changes over those in the control group.

Although the above demonstrations involve only the use of the compound of formula I wherein X is the D-leucyl moiety and R is ethyl, all analogs included in that formula show substantially the same in vivo results. It does appear, however, that the compounds wherein R is ethyl are preferred. The compounds wherein X is a D-aminoacid other than isoleucine are prepared in the same manner as described in Example 1, except for replacing the D-Boc-leucine with the corresponding D-Bos-iso-leucine, D-Boc-alanine, D-Boc-valine, D-Boc-norleucine or D-Boc-α-aminobutyric acid. In these instances, R' of the above moiety —NH—CHR'—CO— contain 1–4 carbon atoms; they are preferred, although R' moieties with 5–7 carbon atoms also show desirable regressions of the male glands in premature and mature animals.

As demonstrated above, the treatment with the compounds of formula I produces significant regressions in the growth of scondary sex organs. For obvious reasons, the results are demonstrated only in animal models; however, rodents have been shown to be reliable models, paralleling glandular development of other warm-blooded animals.

The above defined narrow class of compounds can be used to prevent the development of prostatic hyperplasia and/or to regress prostatic hyperplasia which, to this date, could only be handled surgically. Since these compounds have essentially no toxicity even in doses of 100 mg/kg, and since the doses to be used for successful treatment in animals are in the μg/kg levels, the therapeutic index of the compounds is extremely high. This makes the above treatment an important and unexpected discovery and valuable tool in the management of prostatic disorders. Particularly, the new method can be used to prevent undesirable growth or to reduce the size of an undesirably large prostate, primarily in instances of prostatic hyerplasia. The method is safe and simple, and can be extended over long periods of time without adverse effect on other tissue of the animal.

I claim:

1. The method of reducing or preventing undesirable prostatic growth in a warm-blooded animal consisting essentially of administering to said animal a sufficient daily amount to prevent prostatic growth or to reduce prostate size, of a nonapeptide of the formula L-pGlu-L-His-L-Trp-L-Ser-L-Tyr-X-L-Leu-L-Arg-L-Pro-NH-R wherein X denotes the optically active D-form of an aminoacid moiety of the formula —NH—CHR′—CO— with R′ being a linear or branched carbon chain of 1–4 carbon atoms and wherein R is lower alkyl.

2. The method of claim 1 wherein R′ is isobutyl and R is ethyl.

3. The method of claim 1 wherein said prostatic growth is a prostatic hyperplasia.

4. The method of claim 1 wherein said nonapeptide is administered at a daily parenteral dose of between 1 and 200 μg/kg.

5. The method of claim 4 wherein said parenteral dose is administered as solution in 0.9% of saline.

6. The method of claim 1 wherein said nonapeptide is administered at a daily oral dose of between 2 and 500 μg/kg.

* * * * *